(12) United States Patent
Knutson et al.

(10) Patent No.: US 6,528,697 B1
(45) Date of Patent: Mar. 4, 2003

(54) MODULAR BANDAGE

(75) Inventors: Paul Leslie Knutson, Chaska, MN (US); Scott Douglas Augustine, Bloomington, MN (US); John Paul Rock, Minneapolis, MN (US)

(73) Assignee: Augustine Medical, Inc., Eden Prairie, MN (US)

( * ) Notice: Subject to any disclaimer, the term of this patent is extended or adjusted under 35 U.S.C. 154(b) by 0 days.

(21) Appl. No.: 09/476,554

(22) Filed: Jan. 3, 2000

(51) Int. Cl.[7] .................................................. A61F 13/00
(52) U.S. Cl. ............................ 602/54; 602/42; 602/60; 602/62; 602/63
(58) Field of Search ................................. 602/2, 41–59; 128/888, 889; 607/96, 108, 109, 112, 113–115

(56) References Cited

U.S. PATENT DOCUMENTS

| 1,920,808 A | | 8/1933 | Sander |
| 2,273,873 A | * | 2/1942 | Klein ........................... 602/57 |
| 2,577,945 A | | 12/1951 | Atherton |
| 4,641,643 A | | 2/1987 | Greer |
| 5,213,565 A | | 5/1993 | Rollband |

FOREIGN PATENT DOCUMENTS

| DE | 8815983 | 12/1988 |
| WO | WO 98/46179 | 10/1998 |

OTHER PUBLICATIONS

Communication Relating To The Results Of The Partial International Search Report for PCT/US00/10288.
International Search Report for PCT/US00/10288.

* cited by examiner

*Primary Examiner*—Kim M. Lewis
(74) *Attorney, Agent, or Firm*—Gray Cary Ware & Freidenrich

(57) ABSTRACT

A modular bandage for treating wounds located on highly contoured, non-planar regions of a person includes a stand-off for placement near the wound, and a sheet of material for forming a sealed environment over the wound in conjunction with the standoff. The modular bandage may further include a heater to thermally regulate the sealed environment formed by the standoff and the sheet of material. A sheet of material for such a bandage may include various uniform or compound structures.

12 Claims, 11 Drawing Sheets

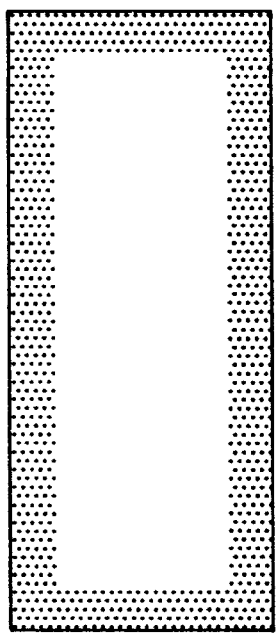
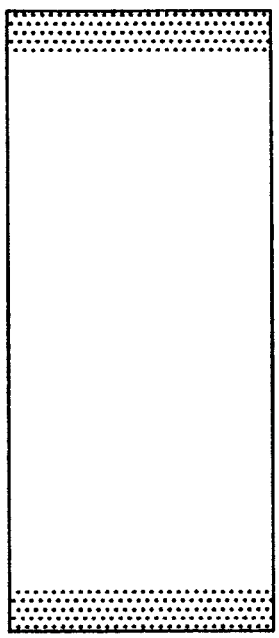
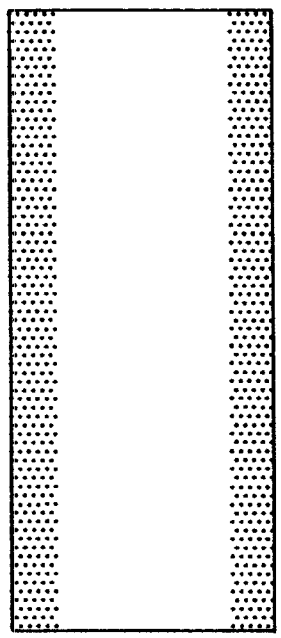
FIG. 10A     FIG. 10B     FIG. 10C
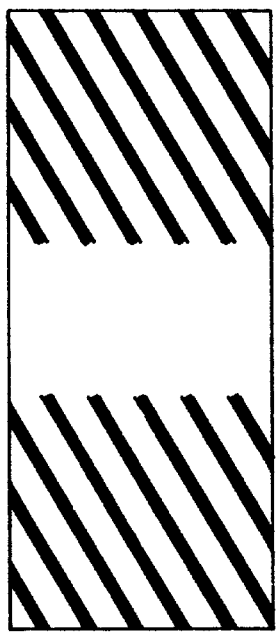
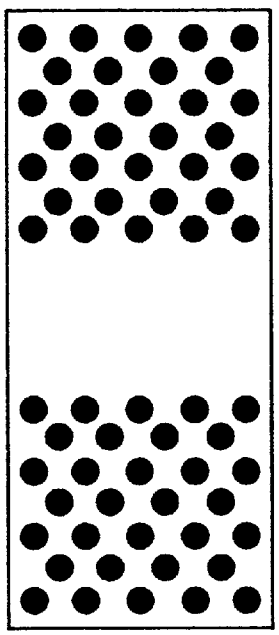
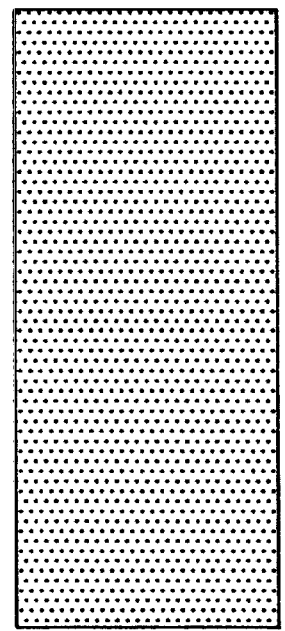
FIG. 10D     FIG. 10E     FIG. 10F

MODULAR BANDAGE

BACKGROUND OF THE INVENTION

1. Field of the Invention

This invention is found in a method and apparatus for treating wounds of a person, in particular, for treating wounds located on extremities or highly contoured, non-planar surfaces of the person.

2. Description of Related Art

In order to prevent or limit infection and shorten the healing process, wounds are commonly covered with sterile bandages. The bandages include gauze that may be held in place over a wound with adhesive tape or other binding means. As noted in a prior, commonly assigned patent, U.S. Pat. No. 5,817,145, gauze bandages have several limitations. First, the gauze bandages do not fully isolate the wound from the surrounding environment and the gauze may adhere to the wound, lengthening the healing process. In addition, the bandages do not thermally regulate the wound environment.

In order to overcome these limitations and others of the prior art, U.S. Pat. No. 5,817,145 teaches a wound treatment device that treats a wound without contacting it. The device includes at least three elements: a wound attachment portion, a standoff portion, and a transition portion. This patent is incorporated by reference for its teachings of such a wound treatment device. The wound attachment portion forms a first plane that is received on the person's skin and includes an adhesive portion for adhering to the person's skin about a wound. The standoff portion defines a second plane above the wound and includes an opening between the first and second planes. The transition portion covers the opening at the second plane, thereby forming a wound treatment volume, connects the attachment portion to the standoff portion and enables the attachment portion to move in conjunction with movement of a person. As described in the '145 patent, each portion is flexible to accommodate movement. While the described wound treatment device is suitable for treating wounds on non-planar surfaces of the person, e.g., the extremities of the person, there may be some highly contoured body portions where its effectiveness might be compromised. Thus, the need exists for a wound treatment apparatus and method for treating wounds located on highly contoured, non-planar surfaces of a person.

SUMMARY OF THE INVENTION

This invention is practiced both as a modular wound treatment apparatus and as a method for treating wounds with such an apparatus. The apparatus is modular in that it comprises separate component parts that may be assembled more or less completely for use. The component parts are a standoff and a strip or sheet of flexible material. At least one surface of the sheet of material has an adhesive material or structure that permits the sheet of material to be attached to the skin, if not also to the standoff. The method includes placing the standoff about or near a wound. The standoff defines or forms a space sufficient to accommodate the wound. Preferably the standoff is flexible, which enables it to conform to the surface area peripheral to the wound ("the periwound"). The method also includes attaching the sheet of material over the standoff, with the adhesive material or structure facing the standoff and skin. The standoff elevates the sheet of material over the wound, forming a treatment volume between itself, the sheet of material and the wound. By this method, the standoff and sheet of material are assembled to form a bandage that provides a sealed environment over the wound. Advantageously, the bandage, when assembled, is entirely or largely out of contact with the wound. This modular bandage and this method of treating a wound are particularly useful when the surface of the person about the wound is non-planar and highly contoured, e.g. when the dermal surface about the wound is located on an extremity of the person. While this description generally references the treatment of a person, it should be understood that the devices described herein may be used in the treatment of animals as well.

The standoff may be formed from an absorbent material, such as foam, in order to support autolytic debridement of a wound. This process is explained in detail in U.S. patent application Ser. No. 09/056,121, filed Apr. 6, 1998, which is commonly assigned with this application, and which is incorporated herein by reference.

In shape and structure, the standoff may be embodied as a single piece of flexible material having a plurality of removable sections. One or more of the sections may be removed in order to provide an opening in the standoff having a shape and area sufficient to surround a wound. In another embodiment, the standoff may include one or more elements placed about or near the wound. In all cases, the role of the standoff is to elevate the sheet of material above and out of contact with the wound.

The sheet of material includes a sheet of flexible material that may have a moisture vapor transmission rate (MVTR). In addition, the sheet of material includes adhesive for attachment onto the surface of the person over the standoff.

Finally, the modular bandage may also include a heater on or in the sheet of material, over the standoff. In this case, the heater is used to regulate the thermal conditions of the wound environment in the treatment volume formed by the standoff and sheet of material. Regulation of the thermal conditions of the treatment volume may, among other objectives, include therapies that target normothermic conditions. Normothermia for the human body can be defined as temperatures in the range of 36° C.–38° C.

BRIEF DESCRIPTION OF THE DRAWINGS

FIGS. 10A–10F are plan views of one surface of the sheet of material showing respective patterns of an adhesive material or structure.

DETAILED DESCRIPTION OF THE INVENTION

Throughout this description, the preferred embodiment and examples shown should be considered as exemplars, rather than as limitations on the present invention.

First Embodiment

Figure 1:
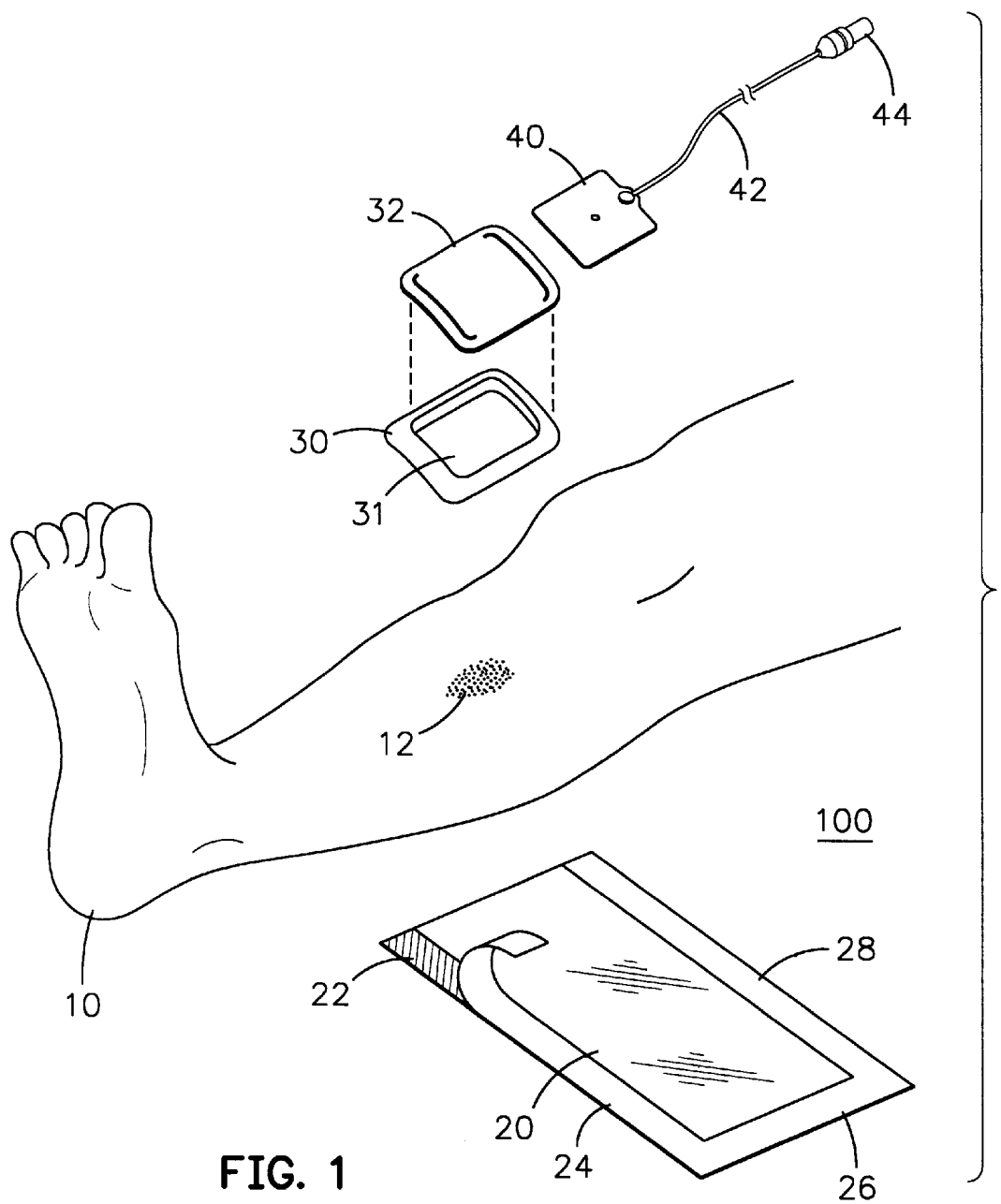
FIG. 1 is an exploded view of a first embodiment of the modular bandage in accordance with the invention prior to deployment over the wound of a person.

FIG. 1 is an exploded view of a modular wound treatment apparatus ("bandage") 100 in accordance with a first embodiment of the present invention prior to deployment on a non-planar surface wound of a person, in particular, prior to the deployment over a wound 12 on the surface of the leg 10 of a person. As shown in FIG. 1, the modular bandage 100 includes at least two modular components: a flexible, sheet-like sheet of material 20 and a flexible standoff 30. Optionally a heater pocket 32, heater 40, heater cable 42, and portable power source 44 may be included. The deployment of the exemplary modular bandage 100 and a more detailed description of the exemplary modular bandage 100 are presented with reference to FIGS. 1 to 4B below. A first step of deploying the modular bandage 100 is placement of the standoff 30 on the surface of the leg 10 surrounding the wound 12 where the surface is the skin of the person.

The standoff 30 is configured to have an inner opening 31 that projects an area greater than the area of the wound 12 on the skin of the person. As described below with reference to FIGS. 5 and 6, the standoff 30 may include a plurality of removable sections so the inner opening 31 of the standoff may be configured for different size wound areas. The standoff 30 includes an adhesive on at least one side for adhering to the skin of the person surrounding the wound 12 to be treated. Further, the standoff 30 may also include an adhesive or other attachment means such as hook and loop, for attaching the standoff to the sheet of material 20. Yet another alternative is providing an adhesive or other attachment means on two sides of the standoff 30 for securing the standoff 30 to both the sheet of material 20 and to the area around the wound 12. The standoff 30 is also relatively flexible so as to be able to conform to highly contoured non-planar surfaces. The standoff 30 may comprise a ring of foam material where the ring may be die cut from a sheet of reticulated polyurethane foam. The ring of the standoff 30 has an opening 31 projecting to an area greater than the area of a wound so that when placed about the wound the opening of the standoff 30 completely encompasses the wound. This enables a non-contact relationship between the ring of the standoff 30 and the wound. In addition, the standoff 30 has a fixed height that is sufficient to maintain the sheet of material off of the wound.

Advantageously, the foam (or equivalent) material of the standoff 30 has particular absorbency properties in order to support autolytic debridement. Further, the standoff may be impregnated with a medicament including an antibiotic, antifungal, or antimicrobial agent. The standoff 30 may also include a deodorant material, nitric oxide releasing materials, or other medicaments capable of accelerating healing or preventing infection. It is understood that the standoff may be made or formed of materials other than foam so long as such materials have similar mechanical properties, in particular having the ability to accommodate motion of a person while maintaining the inner opening formed in the standoff 30. In order to deploy the standoff 30, an adhesive liner (such as liner 60 shown in FIG. 6) may be removed to expose a suitable adhesive (such as adhesive 59 shown in FIG. 6). The standoff 30 is then placed onto the skin of the person so the opening of the standoff 30 accommodates the wound to be treated. It is noted that hair on the skin may be removed prior to the placement of the standoff 30 onto the skin where the hair is located in the region where the adhesive of the standoff 30 may mate with the skin.

In the next step of deploying the modular bandage 100 in accordance with the invention, the sheet of material 20 is placed around the wound 12 of the person and over the standoff 30. In this embodiment, the sheet of material 20 includes a flexible sheet with an MVTR and has a dimension, e.g. a width 26 and/or length 28, sufficient to cover the standoff 30 and provide additional support of the same. For example, the sheet of material is approximately 10 inches wide and 20 inches in length for wounds located on the leg 10 of a person. As shown in FIG. 1, at least one surface of sheet of material 20 includes an adhesive material or structure. In the case of this embodiment one or more adhesive strips, such as the adhesive strip 22, are located on the outer periphery of the sheet of material 20; the adhesive strip 22 includes an adhesive liner 24 to prevent contamination of the adhesive strip 22 prior to deployment around the wound 12.

Figure 2:
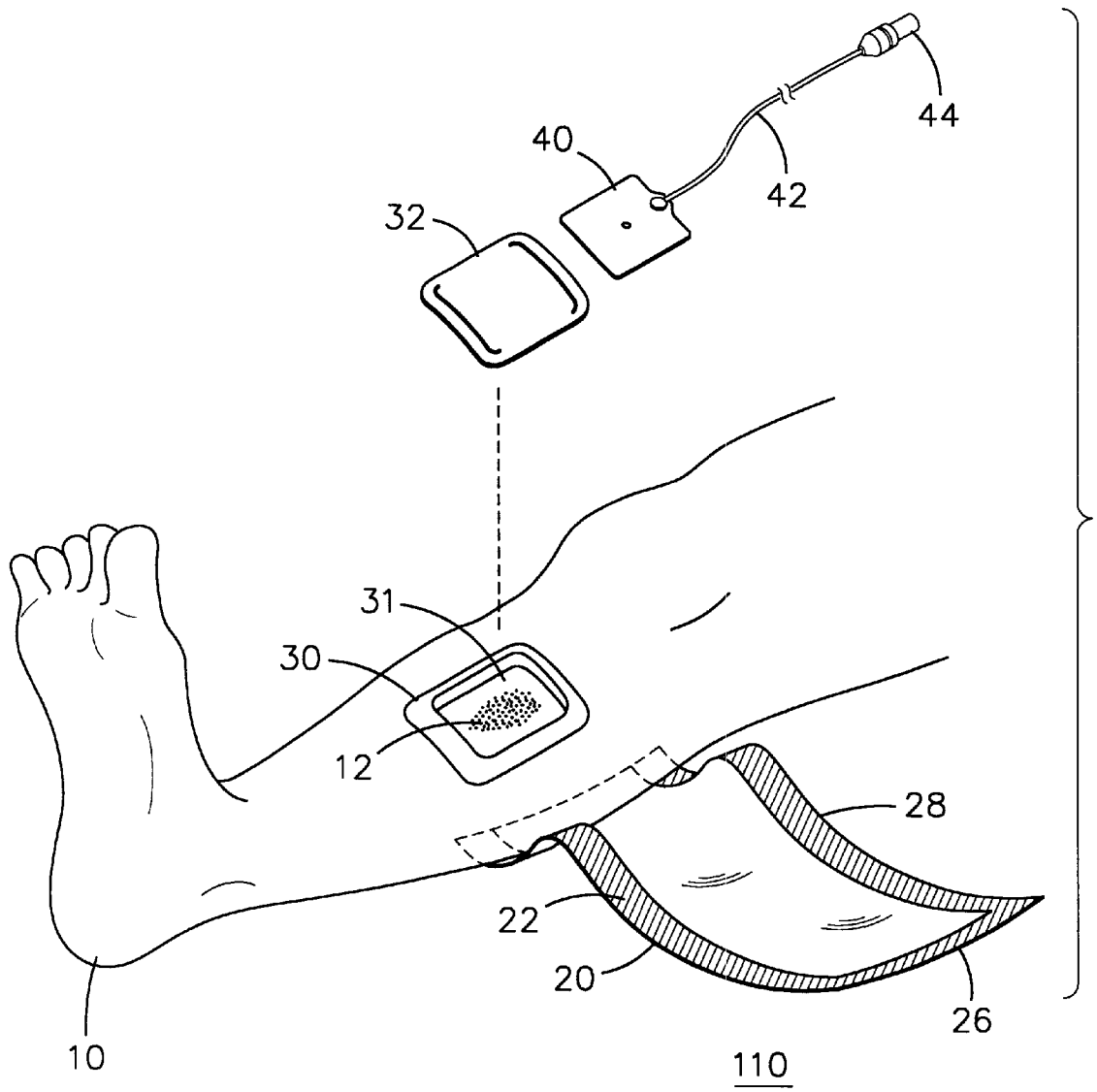
FIG. 2 is another exploded view of the first embodiment shown in FIG. 1 where the standoff has been deployed on the non-planar surface over the wound of the person and the sheet of material is starting to be deployed on the person.
Figure 3A:
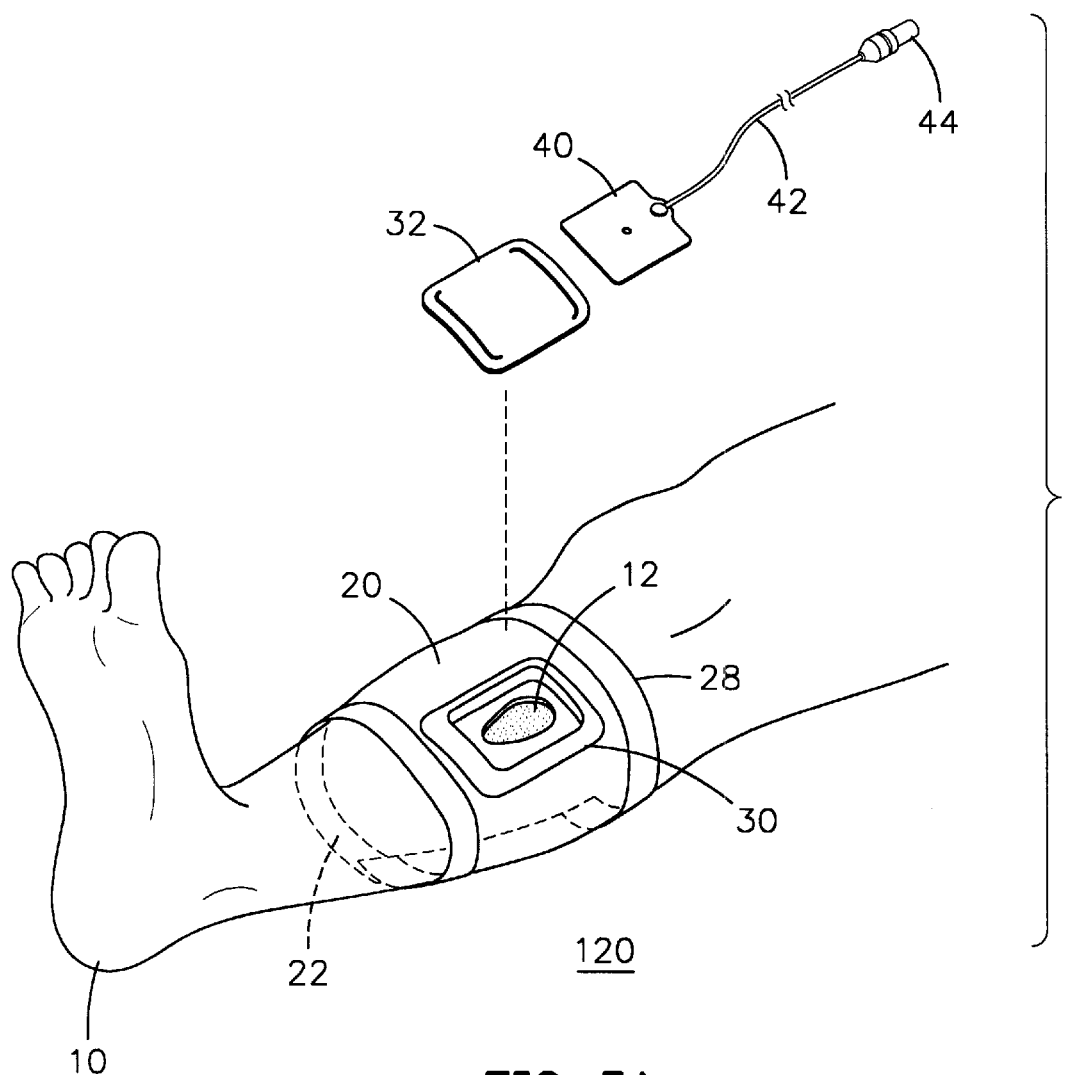
FIG. 3A is another exploded view of the first embodiment shown in FIG. 1 where the standoff and sheet of material have been deployed on the non-planar surface wound of the person.
Figure 4A:
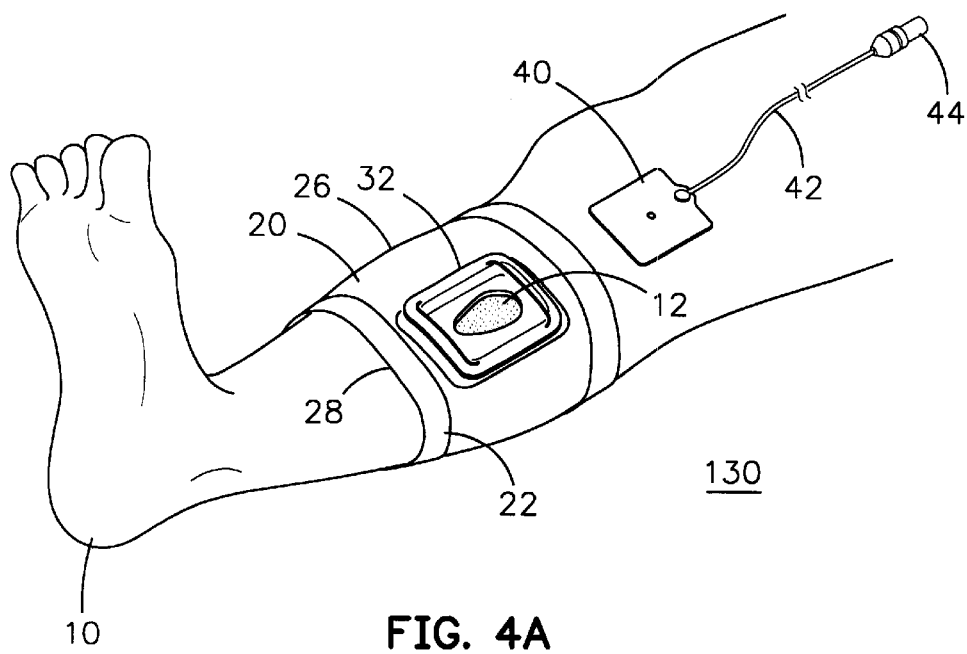
FIG. 4A is a perspective view of the first embodiment shown in FIG. 1 where the standoff and sheet of material, and an optional heater pocket, have been deployed on the non-planar surface over the wound of the person, encircling a limb.

FIGS. 2 and 3A depict an exemplary process of deploying the sheet of material 20. As shown in FIG. 2, the adhesive liner 24 is removed to expose the adhesive strip 22 and then a first section of the sheet of material is attached to the person's skin 12, surrounding the wound. Then, as shown in FIGS. 3A and 4A, the remaining portion of the sheet of material 20 is laid around the circumference of the person's leg 10 outside and over the standoff 30 so a section of the sheet of material 20 overlaps the first deployed section. It is noted that additional hair on the skin of the person may be removed prior to the placement of the sheet of material 20 onto the skin where the hair is located in the region where the adhesive strip 22 of the sheet of material 20 may mate with the skin. The sheet of material 20 of the present invention is configured to serve several functions. First, the barrier section helps maintain the position of the standoff 30 about a wound to be treated. The sheet of material 20 also forms a sealed environment between itself, the openings in the standoff 30, and the wound. It is noted that the sheet of material 20 may move somewhat freely over the standoff 30 to accommodate movement that is likely to be substantial in non-planar deployments, particularly on the extremities of a person. In certain applications, such as smaller wounds, it may be desirable to prevent movement of the sheet of material 20 relative to the standoff 30. This can be accomplished by adhering the standoff 30 to the sheet of material 20 in addition to adhering the standoff 30 to the wound.

Figure 3B:
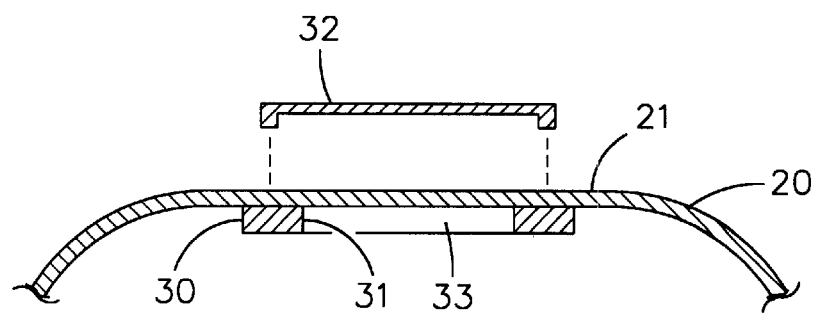
FIG. 3B is a side sectional view showing the sheet of material engaging the standoff.
Figure 4B:
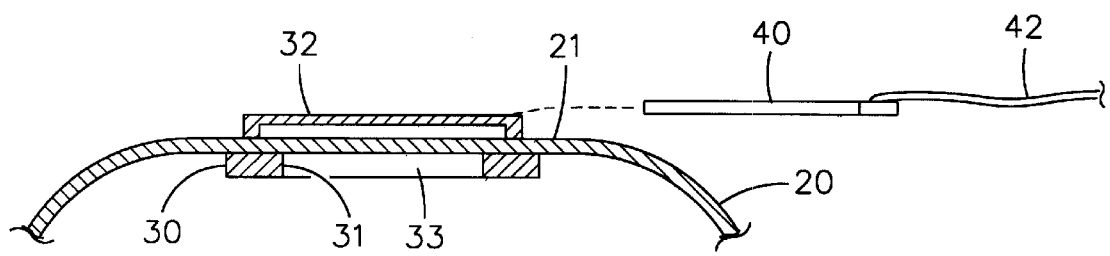
FIG. 4B is a side sectional view showing the optional heater pocket mounted to the sheet of material standoff.

FIGS. 3A and 3B show the standoff mounted or placed over a wound 12, with the sheet of material deployed to secure the standoff and form a wound treatment volume. FIGS. 4A and 4B show a heater pocket mounted to an outer surface of the sheet of material, over the wound volume. None of these figures is to scale; in fact, relative dimensions are exaggerated in order to illustrate particular features and relationships.

In FIGS. 3A and 3B, the standoff 30 is attached about the wound 12 with the opening 31 sized to exceed the wound's periphery. The standoff 30 has been adhered to the skin surface about the wound 12 and the sheet of material 20 has been wrapped around the limb 10, over the top of the standoff 30 so as to form a wound treatment volume 33 in the opening 31, between itself and the wound 12. A particular advantage of this configuration has already been noted in the '145 patent: the wound is protected and covered without being contacted by the modular bandage.

Optionally, as shown in FIGS. 3A, 3B, 4A and 4B, a heater pocket 32 is deployed onto an outer surface 21 of the sheet of material 20 of the modular bandage 100. In FIGS. 3A and 3B, the heater pocket 32 is deployed on the sheet of material 20 with a position substantially over and covering the opening in the standoff 30. Then, a heater 40, such the heater described in the incorporated and commonly assigned U.S. Pat. NO. 5,817,145 may be inserted into the heater pocket 32. As described in U.S. Pat. No. 5,817,145 and U.S. Pat. No. 5,964,723, which are incorporated by reference for their teachings on the heater, the heater 40 is used to maintain a heat per unit area in the wound treatment volume over the wound in order to hasten the wound's healing.

As shown in FIGS. 1 to 4B, the heater 40 is coupled to a portable power source 44 via one or more conductive cables 42 in a preferred embodiment. The portable power source 44 may include one or more batteries connected in series. The portable power source enables ambulatory movement of the person while providing heat to a wound. In other applications, the heater 40 may be coupled to a stationary power source, or the power source may be integrated into the structure of the heater. Of course, the heater 40 may comprise other mechanisms that actively generate and radiate heat into the treatment volume, as well as mechanisms that insulate and reflect heat in the treatment volume.

Figure 4C:
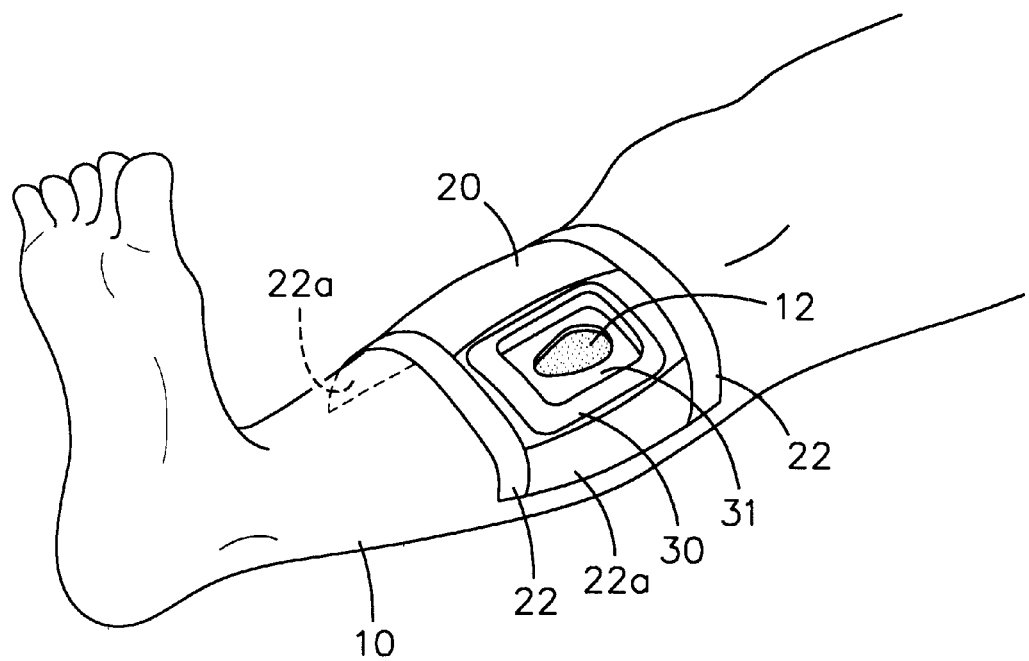
FIG. 4C shows the first embodiment, without an optional heater, and attached to the limb without encircling it.

Finally, with reference to FIG. 4C and with respect to the size of the sheet of material 20 relative to the standoff 30 and the limb, the dimensions of the sheet 20 need be only sufficient to cover the opening 31 and extend far enough to attach to skin outside of the standoff 30, without encircling the limb 10. In this case two strips 22a of adhesive material are disposed on the ends of the surface of the sheet material 20 on which the side strips 22 are disposed.

Figure 5:
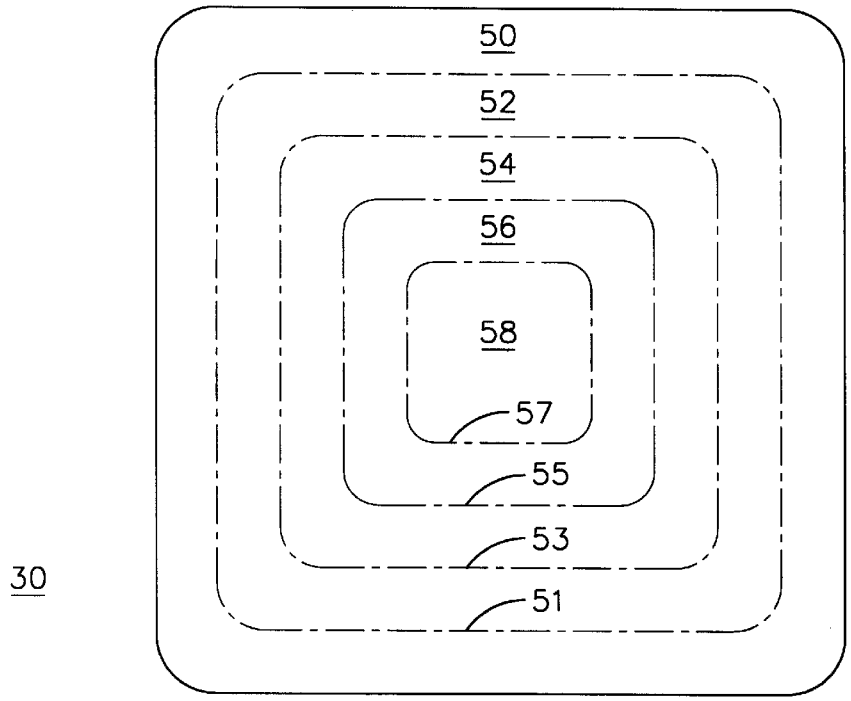
FIG. 5 is a top plan view of an exemplary standoff in accordance with the first embodiment where the standoff includes a plurality of die-cut removable sections to make the standoff configurable for different size wound areas.

As noted above, the standoff 30 may include a plurality of removable sections so the inner area of the standoff may be configured for different size wound areas. First, it is noted that while the standoff 30 shown in FIGS. 1–6 has a rectangular shape, any shape may be used provided the opening of the same accommodates a wound to be treated. For example, the standoff 30 may have a circular, square, or elliptical shape. FIG. 5 is top view of an exemplary view of standoff 30 having four removable sections 58, 56, 54, and 52 surrounded by an outer ring 50. In this embodiment, a semi die-cut section 57, 55, 53, and 51 surrounds each removable section. The semi die-cut sections 57, 55, 53, and 51 enable each section 58, 56, 54, and 52, respectively to be removed from the standoff 30 prior to deployment of the standoff 30 about a wound to be treated. Thus, one or more sections 58, 56, 54, and 52 may be removed prior to deployment of the standoff 30 as a function of the area and shape of the wound to be treated.

Figure 6:
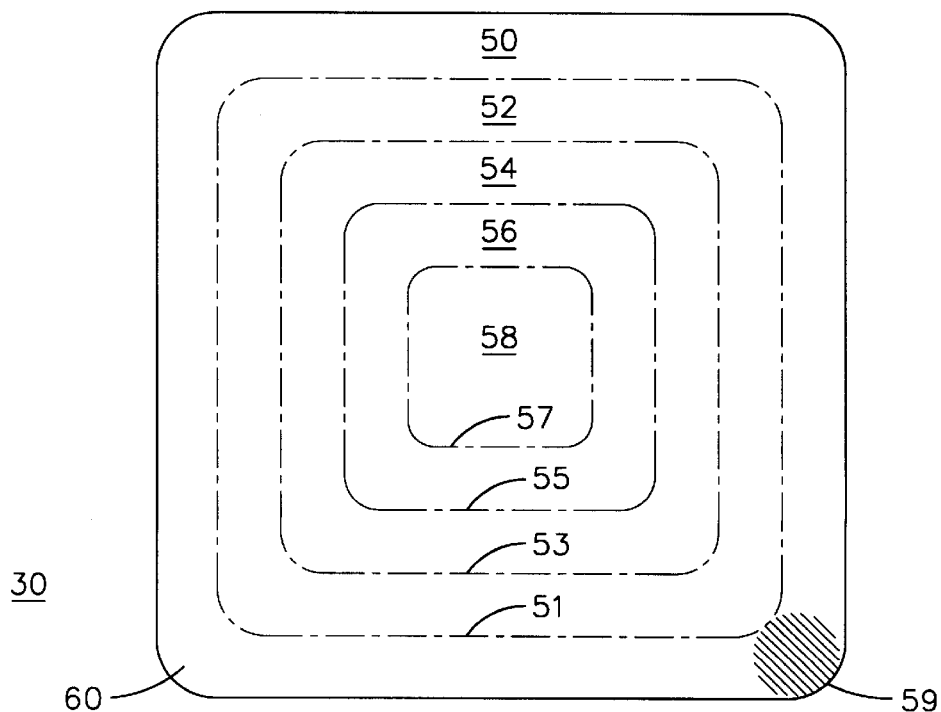
FIG. 6 is a bottom plan view of the exemplary standoff shown in FIG. 5 where each section of the standoff has an adhesive layer covered by an adhesive liner.

A bottom view of the exemplary standoff 30 is shown in FIG. 6. As shown in this FIGURE, the standoff 30 includes an adhesive layer 59 and adhesive liner 60. As also shown in FIG. 6, the adhesive liner 60 is also semi die-cut so that when one or more sections 58, 56, 54, and 52 is removed from the standoff 30, the corresponding section of the adhesive liner 60 is also removed. As noted above, the standoff 30 may be comprised of foam or any other material having the appropriate properties according to the present invention. Accordingly, it is to be understood that the invention is not to be limited by the specific illustrated embodiments, but only by the scope of the appended claims.

Second Embodiment

Figure 7A:
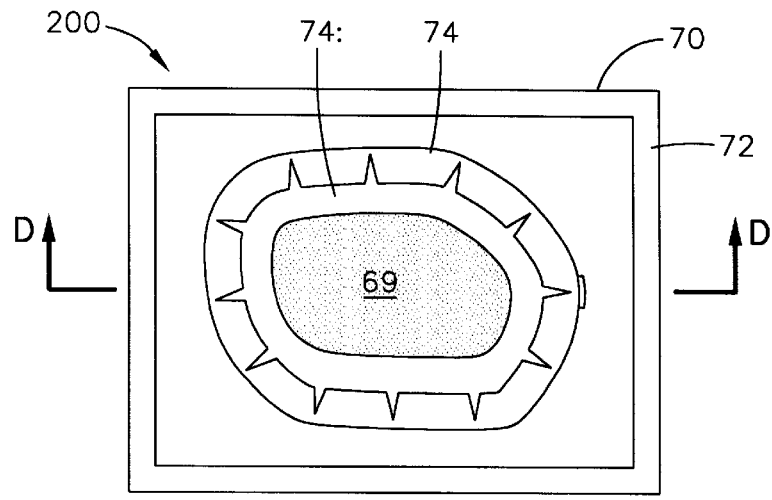
FIGS. 7A–7D illustrate a second embodiment of the modular bandage in accordance with the invention, with FIG. 7A showing the second embodiment deployed over a wound, FIG. 7B showing a perspective view of a member from which the standoff is formed, FIG. 7C showing a cross-sectional view of the member taken along CC in FIG. 7B, and FIG. 7D showing a side sectional view of the second embodiment taken along DD in FIG. 7A.
Figure 7B:
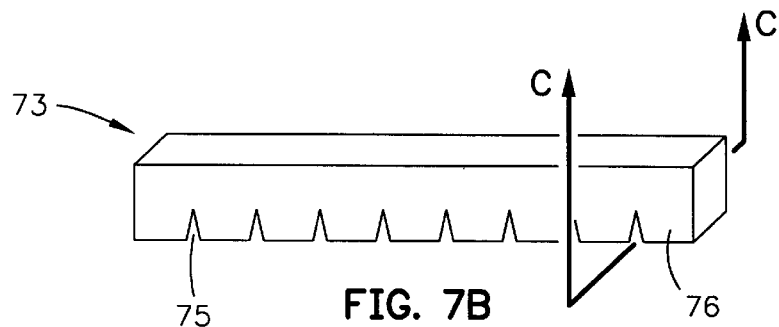
Figure 7C:
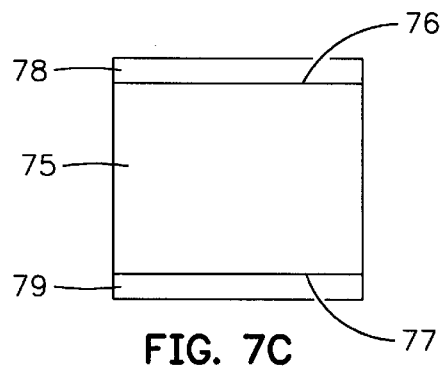
Figure 7D:
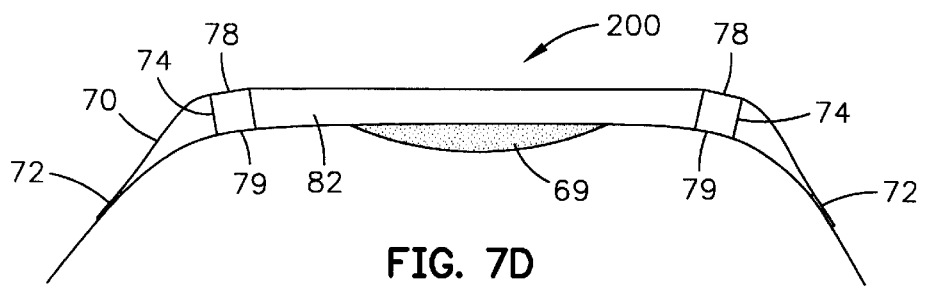

Refer now to FIGS. 7A–7D which together illustrate a second embodiment of a modular bandage 200 according this invention. In the second embodiment, the modular bandage 200 includes a standoff and a sheet of material. A linear strip of foam material (indicated by reference numeral 73 in FIG. 7B) is deformed or flexed into a standoff 74 having configuration with an inner opening 74i that encloses an area greater than the area of a wound 69 on the skin of a person. A sheet of material 70 having adhesive or an adhesive structure around or near the periphery of the sheet of material 70 in a pattern 72 on at least one of the surfaces of the sheet of material 70. The material of which the linear strip 73 is made can comprise, for example, a foam material and the strip may be provided with notches such as the notches 75 to facilitate the deformation or bending of the strip 73 into the shape of the standoff 74. The linear strip 73 is oriented with respect to the wound 69 in the following manner. The surface into which the notches 75 are cut face toward the wound 69 (or it may face away from the wound), the surfaces 76 and 77 that are perpendicular to the surface having the notches 75 face the material sheet 70 and the skin of the person, respectively. As shown in FIG. 7C, an adhesive or an adhesive structure 78 is carried on the surface 76 and an adhesive or adhesive structure 79 is carried on the surface 77. The adhesive or adhesive structures 78 and 79 are provided so that the standoff 74 may be fixed adhesively to the skin of the person and also to the sheet of material 70. The linear strip 73 is preferably formed from an absorbent material such as foam in order to support autolytic debridement from the wound 69. In this regard, the surface of the linear strip 73 that faces the wound 69 would preferably be in a condition to receive and absorb moisture such as wound exudate into the material of the linear strip 73, while the opposing surface (that which faces outwardly, away from the wound) would be "skinned" or otherwise processed in order not to leak moisture. As FIG. 7D illustrates, the standoff 74 has a height that maintains the material sheet 70 off of, or away from the wound 69, forming a wound treatment volume 82 over and about the wound 69 and the periwound. The standoff 74 is held in place about the wound by the adhesive or adhesive structure 79 acting against the skin. The sheet of material 70 is held in place by the adhesive or adhesive structure 72 around its periphery and may be further secured by the adhesive or adhesive structure 78 that acts between it and the standoff 74. Although not shown, a heater may be deployed above the wound 69.

Third Embodiment

Figure 8A:
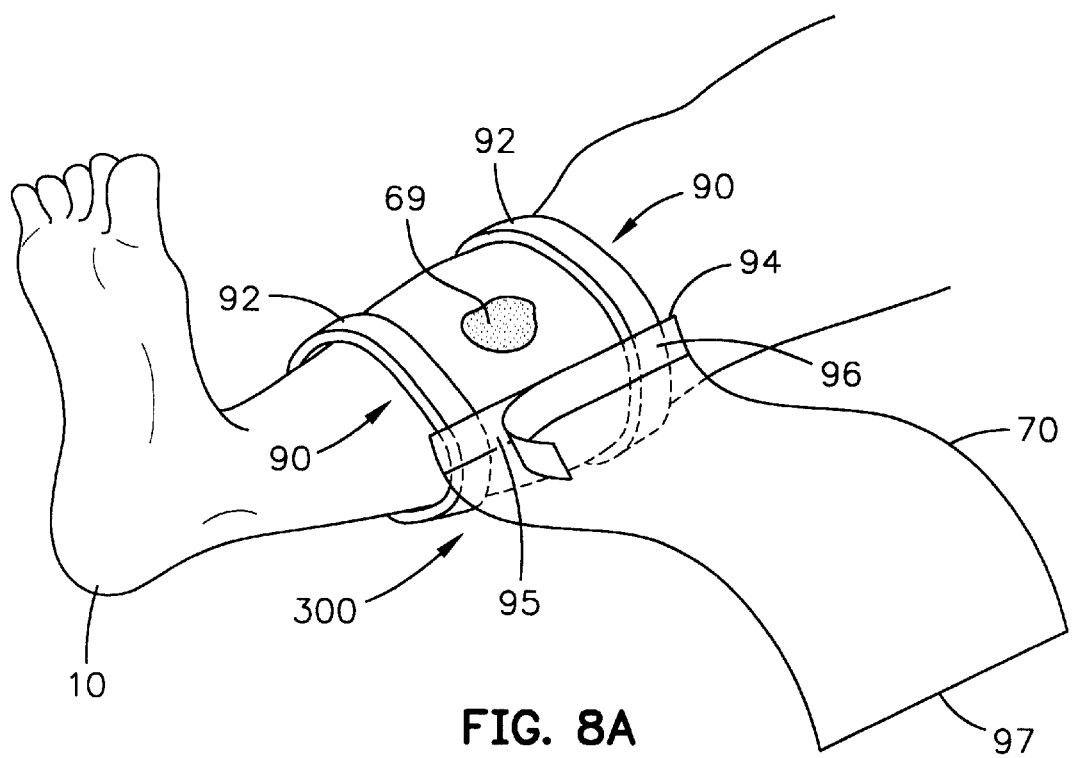
FIGS. 8A–8D illustrate a third embodiment of the modular bandage in accordance with the invention.
Figure 8B:
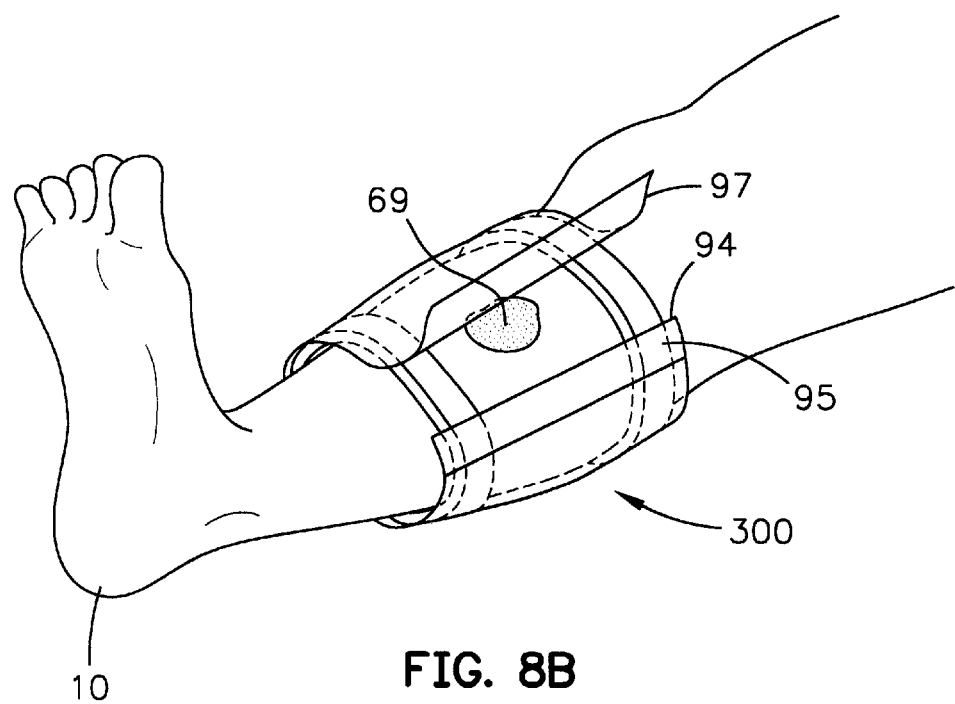
Figure 8C:
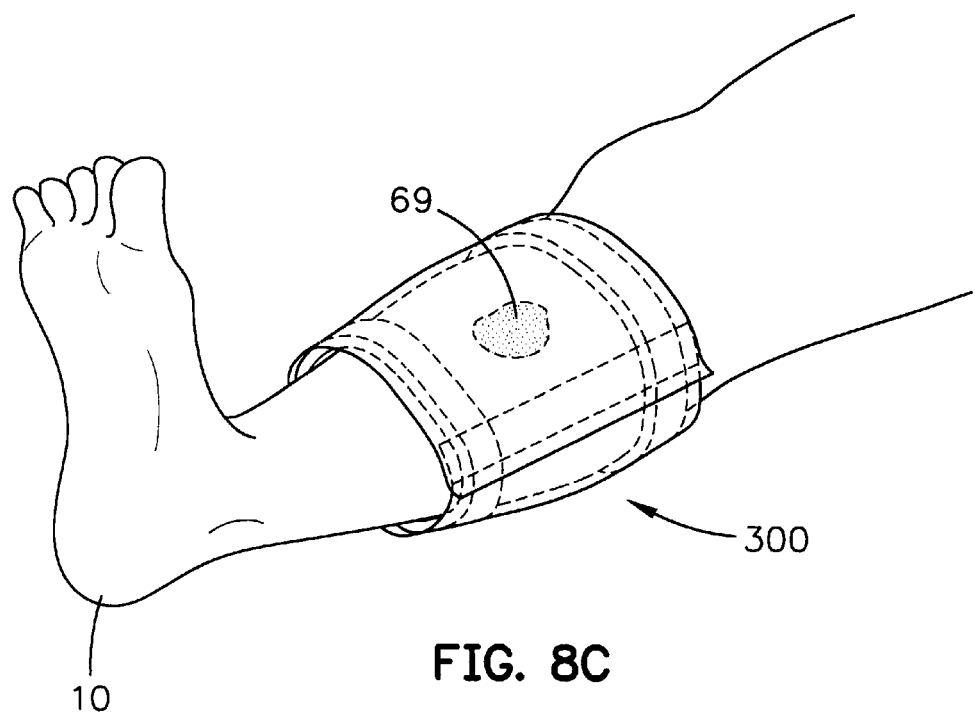
Figure 8D:
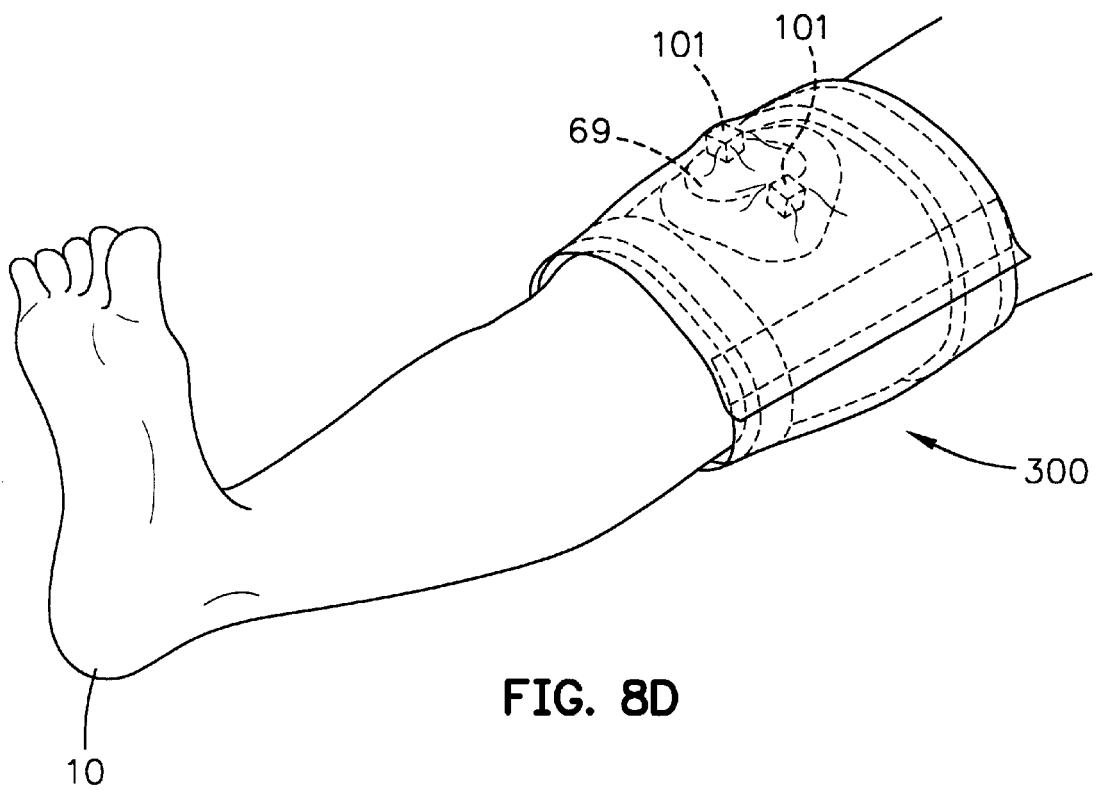

Refer now to FIGS. 8A–8D for an understanding of a third embodiment of the modular bandage 300 according to this invention. In these figures, the modular bandage 300 includes a standoff and a sheet of material 70 having two ends 94 and 97 and an adhesive or adhesive structure 95 on one surface near the end 94. The standoff comprises two or more members such as the linear strips 90 that deformation bend to partially or completely encircle a limb, on either side of a wound. For example, the strips may have the structure and composition of the strip 73 illustrated in FIG. 7B, with the following exception. In FIGS. 8A–8D, each of the linear strips 90 is oriented such that the notched surface either faces the skin or faces in a direction opposite the skin. Further, adhesive is applied to the surface with the notches 75 and to the opposite surface indicated by reference numeral 75o in FIG. 7B. The two linear strips 90 are deformed or bent so as to conform to and to be disposed on the limb. The strips 90 are placed on either side of the wound 69 such that one surface with an adhesive or an adhesive structure faces the skin, while the opposing surface, indicated by reference numeral 92 for each of the strips 90 in FIG. 8A, faces the sheet of material 70, providing for the adherence of the sheet of material 70 to the now deformed strips 90. As FIGS. 8A–8D show, the sheet of material 70 has a width sufficient to span the distance between the strips 90 and a length sufficient to encircle the limb so that the end 97 is brought against and adhered to the adhesive or adhesive structure 95 when the detachable strip of material 96 is removed from the sheet of material 70. In this embodiment, the wound treatment volume is the space that lies between the sheet of material 70 and the skin of the limb and between the linear strips 90. As shown in FIG. 8D, the standoff structure can be augmented or supplemented by individual blocks or posts 101 of material having adhesive or adhesive structures on opposing sides so that they may be adhered to the skin near the wound and to the sheet of material.

Figure 9:
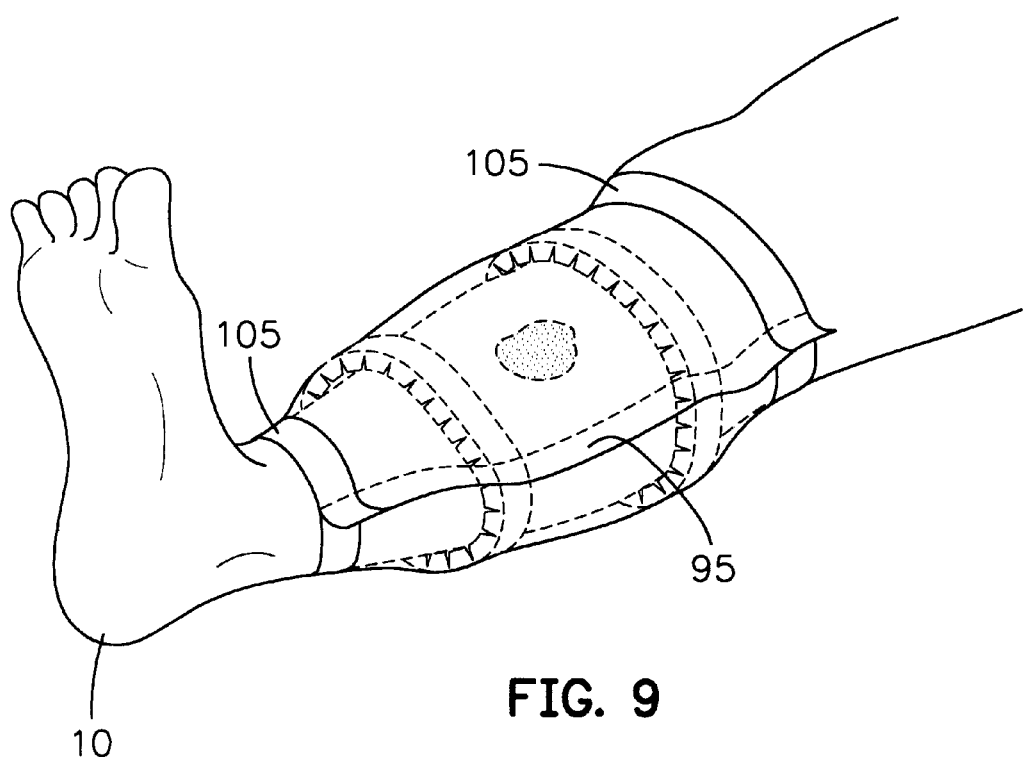
FIG. 9 illustrates a variation of the third embodiment of the modular bandage.

FIG. 9 illustrates a variation of the third embodiment in which the width of the sheet of material 70 is such that its sides extend beyond the elements 90 of the standoff and have adhesive or adhesive structures on a surface that faces the skin of the limb.

Sheet of Material

Six views of patterns of adhesive material or structures for the sheet of material in any embodiment of a modular bandage according to this invention are shown in FIGS. 10A–10F. The views are in plan and show the surface of the sheet of material (20, 70) that faces the standoff and skin in the vicinity of a wound being treated with the modular bandage. In each view, adhesive materials or structures are indicated by shadings. In FIG. 10A, adhesive material or an adhesive structure is in the pattern of an open frame that follows and lies near the periphery of the sheet of material 20. In FIG. 10B, the pattern locates adhesive material or structures in strips near the ends of the sheet of material, in FIG. 10C, in strips near the sides. In FIG. 10D, the pattern, repeated at the ends, is a rectangular area formed by slanted strips; in FIG. 10E the rectangular patterns are formed by dots. In FIG. 10F, an adhesive material or structure occupies the entire surface.

The sheet of material (20, 70) may be formed of many sheet-like materials that generate a breathable, sealed environment with the standoff. Some examples of these materials include polyester, polyamide, polyethylene glycol terephthalate, metal foils, and ionomer resins, polyolefin, polyethylene, polypropylene, polyvinyl chloride (PVC), polyurethane, and ethyl vinyl acetate (EVA) co-polymer. Further, although a single sheet, layer, or film is shown, the sheet of material may, in fact, have a more complex structure of layers and materials. Such structures and materials may be selected in combinations that achieve desired functional and/or clinical objectives. Additionally, the sheet of material may be microperforated in part for enhanced vapor transmission or may be of composite construction to allow for varying degrees of permeability along its surface. For example, it may be desirable to have a portion of the sheet of material with a higher MVTR for the area extending outside the margin of the standoff, to avoid excess accumulation of moisture around the healthy skin. In addition, the sheet of material may have a different shape and size while still providing a sealed environment between the standoff, the wound, and its inner surface.

Various structures for the sheet of material in any embodiment of a modular bandage according to this invention are shown in FIGS. 11A–11H. These figures are subdivided into two groups: 11A–11D and 11E–11H. The first group illustrates various structures and material compositions of which the sheet of material may be formed. FIGS. 11E–11H illustrate various configurations in combining a heater with a sheet of material.

Figure 11A:
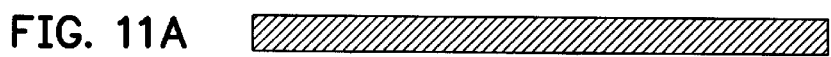
FIGS. 11A–11D are side sectional views showing four respective structures and compositions of the sheet of material.
Figure 11B:
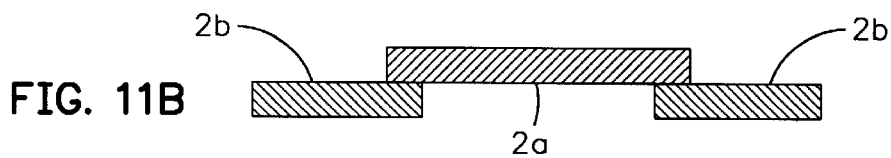
Figure 11C:
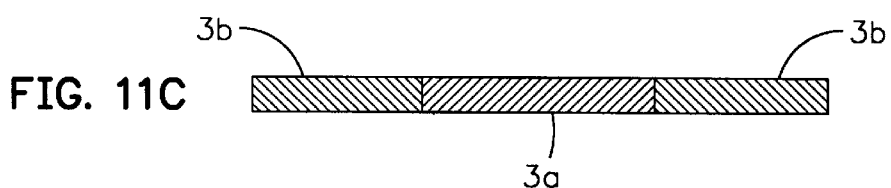

Taking the group that includes FIGS. 11A–11D, FIG. 11A shows a sheet of material comprising a single layer of a substantially uniform composition. This uniform construction may be sufficient for many smaller wounds that have no special complications. FIG. 11B shows a sheet of material embodied as a unitary structure comprising separate layers with two lateral layer members (2b) that are generally coplanar but spaced apart to define a central opening over which a third layer member (2a) that spans the two lateral layer members is positioned. FIG. 11C shows a sheet of material embodied as a unitary structure in the form of compound layer having lateral layer members (3b) disposed on either side of a central layer member (3c).

With reference to FIGS. 11B and 11C, many functional and/or clinical objectives can be realized with these compound structures. For example, in treating a wound on a patient suffering from venous disease it may be advantageous to provide a sheet that is a combination of Coban® material (2b, 3b) and polyurethane material (2a, 3a). Patients suffering from venous disease require assistance in the form of compression for aiding in the venous return of fluids from their lower extremities. These patients frequently suffer from ulcers on these extremities. As shown in FIG. 11B, for example, the sheet may include two elastic lateral layer members 2b of Coban® material and a third, relatively non-elastic, member 2a of polyethylene material where the Coban® material is used beyond the margins of the standoff portion in order to effect a compressive force on the relatively healthier tissues outside the wound margin. The polyurethane material then would be disposed over the standoff providing the proper barrier layer to protect the wound. This configuration would also work well for an unusually large wound in that the elastic portions (2b) of FIG. 11B would enable stretching and uniform tensioning of the plastic film portion (2a) to ensure the film maintains a non-contact position over the span of the standoff surrounding such a wound.

Another example of the functionality of these combinations is in the application to a burn injury. Severe burns may have a gradation of insult resulting in some areas of significant damage surrounded by less damaged, but still sensitive skin. In this case, a compound sheet of absorbent material combining a hydrogel material (2b, 3b) and a low MVTR radiation reflective (also relatively non-elastic) material may be utilized. This combination may be formed by either overlaying the two materials, see FIG. 11B, or by a compound layer formed by coextrusion as shown in FIG. 11C. In the case of a coextruded material sheet, the hydrogel material (3b) of FIG. 11C can be used for the area beyond the margin of the standoff, in contact with the periwound area to keep it moist and protected from infection. The low MVTR reflective material (3a) of FIG. 11C would protect the severely wounded portion inside the standoff area keeping the environment moist and normothermic.

Yet another application is in the field of veterinary medicine where it may be impractical or undesirable to shave large portions of a subject's skin surface. Here a composite sheet arrangement as shown in FIG. 11B would include as self-adhering elastic wrap (2b) and a relatively non-elastic microperforated film (2a). This combination would enable the clinician to cover the wound over the standoff and wrap the peripheral material around the patient's body or extremity without having to directly attach the material (2b) to the skin of the subject.

Figure 11D:

FIG. 11D shows a monolayer structure with microperforations. This construction can be for application to large wound areas where the excess accumulation of moisture in the wound and the surrounding tissues is of concern.

Table I gives various exemplary material compositions for the numbered elements of these figures. It is contemplated that the materials exhibited in the table may be combined in numerous different ways in order to meet a variety of clinical objectives.

TABLE I

| 1 | 2a | 2b | 3a | 3b | 4 |
|---|----|----|----|----|----|
| Polyester | Polyester | Polyester | Polyester | Polyester | Microperforate materials |
| Polyamide | Polyamide | Polyamide | Polyamide | Polyamide | |
| Polyethylene glycol terephthalate | Polyethylene glycol terephthalate | Polyethylene glycol terephthalate | Polyethylene glycol terephthalate | Polyethylene glycol terephthalate | |
| Ionomer resins | Ionomer resins | Ionomer resins | Ionomer resins | Ionomer resins | |
| Polyolefin | Polyolefin | Polyolefin | Polyolefin | Polyolefin | |
| Polyethylene | Polyethylene | Polyethylene | Polyethylene | Polyethylene | |
| Polypropylene | Polypropylene | Polypropylene | Polypropylene | Polypropylene | |
| Polyvinyl chloride | Polyvinyl chloride | Polyvinyl chloride | Polyvinyl chloride | Polyvinyl chloride | |
| Polyurethane | Polyurethane | Polyurethane | Polyurethane | Polyurethane | |
| Ethyl vinyl acetate co-polymer | Ethyl vinyl acetate co-polymer | Ethyl vinyl acetate co-polymer | Ethyl vinyl acetate co-polymer | Ethyl vinyl acetate co-polymer | |
| Hydrogel | Micro-perforated any of the above | Micro-perforated any of the above | Micro-perforated any of the above | Coban Elastic wrap Woven bandage material Gauze material (incl. wovens and non-wovens) Lyofoam Hydrogel | |
|  |  | Coban Elastic wrap Woven bandage material Gauze material (incl. wovens and non-wovens) Lyofoam Hydrogel |  |  |  |

Coban ® is a self-adherent elastic wrap which 3M makes under part number MMMH1583.
Lyofoam ®, a Seton Healthcare Group product is a felted foam dressing material. (Upper surface is open cell, lower has been "felted" resulting in minimal porosity, like a skin surface.)
Hydrogel sheets may be obtained from Smith and Nephew under the tradename Flexigel ™.

Figure 11E:
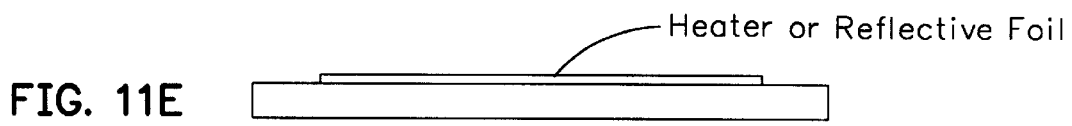
FIGS. 11E–11H are side sectional views showing four respective arrangements for locations of the optional heater.
Figure 11F:
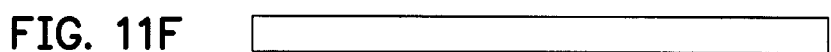
Figure 11G:
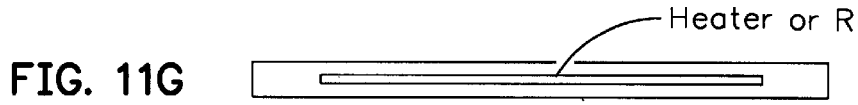
Figure 11H:
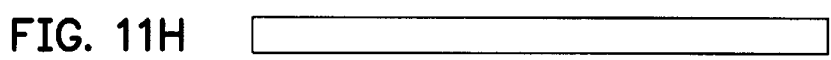

With reference to FIGS. 11E–11H, various heater configurations that are optionally practiced with this invention may be understood. As an alternative to a pocket, the heater may be detachably retained on upper or lower surfaces of the sheet of material by an adhesive layer, hook and loop fasteners, tape, or other commonly known attachment mechanisms that would act between the sheet surface and the heater. This is shown in FIGS. 11E and 11F. As a further alternative, the heater could be integral in construction with sheet of material; this is shown in FIG. 11G. In FIG. 11H, the heater is simply a layer of heat reflective material that consists of the sheet of material itself. The optional heater may also include or consist of a heat reflective metal foil section for placement over the wound treatment volume using any of the constructions shown in FIGS. 11E–11G.

Heater constructions may include:
Electrically conductive textiles such as those manufactured by Gorix Ltd., Birkdale, Southport, UK;
Heat reflective materials such as polyethylene glycol terephthalate (Mylar®, made by Dupont);
Phase change materials;
Resistive wire heaters; or
Chemical packets (e.g. iron oxide).

Clearly, the other embodiments and modifications of this invention will occur readily to those of ordinary skill in the art in view of these teachings. Therefore, this invention is to be limited only by following claims, which include all such embodiments and modifications when viewed in conjunction with the above specification and accompanying drawings.

What is claimed is:

1. A method for treating a wound, the method comprising:
providing a flexible standoff having a plurality of removable sections;
removing one or more of the plurality of removable sections from the standoff to form an opening in the standoff;
placing the flexible standoff near the wound such that the shape and area of the opening completely surround the wound; and
attaching a flexible sheet of material over the standoff and to skin near the wound to form a treatment volume about the wound.

2. The method according to claim 1, wherein the sheet of material further includes an adhesive strip for attaching the sheet of material to the surface of the person about the wound.

3. The method according to claim 2, wherein the sheet of material has at least one dimension sufficient to encircle the extremity of the person when deployed on the extremity, the method further including at least partially encircling the extremity with the sheet.

4. A method according to claim 1 further comprising:
placing a heater onto a surface of the sheet of material.

5. The method according to claim 1, further including actively heating the treatment volume.

6. A modular bandage for treating a wound, the bandage comprising:
a standoff with an outside margin and an adhesive on at least one surface;
the standoff including a plurality of removable sections, one or more of the plurality of removable sections for being removed to form an opening in the standoff having an area greater than the area of the wound;
a flexible sheet of material for extending over and outside the margin of the standoff; and,
an attachment means for attaching the sheet to skin outside the margin of the standoff.

7. The bandage of claim 6, wherein the attachment means is an adhesive.

8. The bandage of claim 7, wherein the flexible material sheet includes two lateral edges and two ends.

9. The bandage of claim 8, wherein the adhesive is located on at least one of the ends.

10. The bandage of claim 8, wherein the adhesive is located on at least one of the ends and at least one of the edges.

11. The bandage of claim 7, wherein the adhesive has a pattern.

12. The bandage of claim 11, wherein the sheet includes a portion void of adhesive.

* * * * *